United States Patent [19]

Curry et al.

[11] 4,168,144

[45] Sep. 18, 1979

[54] KERATINOUS FIBERS COLORANT COMPOSITIONS CONTAINING BASIC DYES AND AN ANIONIC-CATIONIC DETERGENT COMPLEX

[75] Inventors: Kenneth V. Curry, Camberley; Guy A. G. Ricketts, Teddington, both of England

[73] Assignee: Lever Brothers Company, New York, N.Y.

[21] Appl. No.: 595,462

[22] Filed: Jul. 14, 1975

Related U.S. Application Data

[63] Continuation of Ser. No. 419,557, Nov. 28, 1973, abandoned, which is a continuation of Ser. No. 195,012, Nov. 2, 1971, abandoned.

[30] Foreign Application Priority Data

Nov. 6, 1970 [GB] United Kingdom ............... 52910/70

[51] Int. Cl.$^2$ ................................................ A61K 7/13
[52] U.S. Cl. ........................................... 8/10.1; 8/10; 8/84; 8/85 R; 8/89 R; 8/93; 424/70
[58] Field of Search ................. 8/10, 10.1, 84, 85, 8/89, 93; 424/70

[56] References Cited

U.S. PATENT DOCUMENTS

| | | | |
|---|---|---|---|
| 2,695,259 | 11/1954 | Charle | 8/10.1 |
| 2,922,690 | 1/1960 | Muller et al. | 260/158 |
| 2,928,772 | 3/1960 | Anderson | 424/70 |
| 2,940,902 | 6/1960 | Vorsatz | 424/70 |
| 2,983,651 | 5/1961 | Seemuller | 8/10.1 |
| 3,179,483 | 4/1965 | Mellon | 8/84 |
| 3,194,735 | 7/1965 | Brechner | 8/10.1 |
| 3,369,970 | 2/1968 | McLaughlin et al. | 8/10.1 |

FOREIGN PATENT DOCUMENTS

1050791 12/1966 United Kingdom.

*Primary Examiner*—James O. Thomas, Jr.
*Assistant Examiner*—Vera C. Clarke
*Attorney, Agent, or Firm*—Kenneth F. Dusyn

[57] ABSTRACT

This specification is concerned with a hair colorant composition in which the dyestuffs are basic dyes. The composition is made high foaming by the incorporation of an anionic:cationic detergent complex. A typical example of such a composition has the following formulation:

| | % by weight |
|---|---|
| Basic dyestuff | 2.8 |
| Potassium laurate | 2.3 |
| Lauryl trimethyl ammonium bromide | 5.4 |
| Targitol NP 35 (a nonionic surfactant) | 6.0 |
| Isopropanol | 10.0 |
| Thickener | 3.2 |
| Water | to 100 |

Such a composition when formulated as described has been found to give high foaming with good intensity dyeing even in the darker shades, even dyeing and good coverage of hair containing as much as 15 to 25% grey.

4 Claims, No Drawings

KERATINOUS FIBERS COLORANT COMPOSITIONS CONTAINING BASIC DYES AND AN ANIONIC-CATIONIC DETERGENT COMPLEX

This is a continuation, of application Ser. No. 419,557, filed Nov. 28, 1973, now abandoned, which in turn is a continuation of application Ser. No. 195,012, filed Nov. 2, 1971, also abandoned.

This invention relates to compositions for dyeing keratinous fibres and more particularly to hair colorants.

Semi-permanent colorants which are removed over a period of a few weeks by normal regular shampooing are now quite popular. Factors contributing to this popularity are that the colorants are formulated as "one pack" systems and are thus simple to apply and that a detergent is normally included in the composition, giving a foaming product similar to a conventional shampoo.

A disadvantage of this colorant system is that till now it has not been possible to achieve satisfactory products which will impart darker shades such as dark brown and black to the hair.

For many years it has been realized that a wide range of shades can be obtained by the deposition of cationic or basic dyestuffs onto the hair. However, it has been suggested that basic dyes can produce uneven dyeing of the hair (see J.Soc.Cos.Chem. 20, 595–602).

One of the difficulties in formulating shampoos containing cationic materials is that, in general, cationic materials are incompatible in solution with anionic detergents but that the presence of anionic detergents is necessary to provide the large amounts of lather which the consumer expects of a shampoo system. Various attempts at avoiding the problem set by the general incompatibility of cationic dyestuffs and anionic detergents have beem made. For instance, U.S. Pat. No. 2,763,269 (Rayette Inc.) describes compositions including basic dyes in combination with nonionic surfactants. However, we have found that colorants employing nonionic surfactants as the sole detergent-active compound of the shampoo base do not give a sufficiently large volume of foam to satisfy the modern consumer. In another proposal, described in British Pat. Specification No. 986,712 (Cheseborough-Pond's Inc.), basic dyes are combined with amphoteric surfactants. Although this system gives an adequate foam volume we have found that, generally, basic dyes are unstable in an amphoteric medium. This instability results in fading of the colors of the dyes which not only produces an overall lowering in intensity but, in a blend of dyestuffs, can change the color of the dyeing composition and give off-shades.

We have now discovered, surprisingly, that basic dyestuffs are compatible in solution with high-foaming anionic-cationic detergent complexes, e.g. of the types described in British Pat. Specification No. 1,050,791, and that a composition comparing a combination of a basic dyestuff and an anionic-cationic detergent complex is stable, capable of providing a satisfactory volume of foam and effective to an unexpected degree, not only in coloring virgin hair, but also in providing level dyeing on hair that has been permanently waved and in covering the greyed hair containing 15-25% of grey.

Accordingly, the present invention provides a high foaming composition for dyeing keratinous fibres comprising a solution of an anionic-cationic detergent complex and a basic dyestuff.

By the term "a high foaming composition" is meant a composition which, when dissolved in hard tap water to provide a solution containing shampoo in an amount of 5% weight by volume, produces a specific volume of foam of at least 8 cc/gm as determined in a modification of the "Mixmaster" test described by J. M. Bromley in J.Soc.Cos.Chem. 15, 631-639 (1964). The modification referred to is that we have diluted our detergent solution to 10% and we have operated at room temperature.

The following table illustrates the specific foam volume obtained from 5% by weight active solutions in tap water (pH 7) of various anionic-cationic detergent complex systems containing detergents in various molar ratios, 10% by weight of isopropanol and Maxilon Blue GRL 500% at a level of 0.4% by weight. It can be seen that for the system potassium soap-trimethyl alkyl ammonium salt, a great improvement in foam volume is obtained by the use of the detergent complex over the use of either of its components alone. For example, the foam volume of 5.9 cc/gm for the $C_{12}$ soap alone indicates that the foam collapses in tap water.

Table 1

| Effect of molar ratio (based on soap + fatty acid) on foam volume | | | | | |
|---|---|---|---|---|---|
| alkyl chain length of anionic : cationic potassium : trimethyl alkyl soap : ammonium salts | Foam volume at different molar ratios anionic : cationic (cc/gm) | | | | |
| | 100:0 | 60:40 | 50:50 | 40:60 | 0:100 |
| $C_8 : C_{12}$ | — | 12.6 | 11.1 | 12.3 | 5.7 |
| $C_8 : C_{16}$ | — | 8.7 | 11.3 | 11.4 | 7.5 |
| $C_9 : C_{12}$ | — | 13.2 | 13.1 | 12.9 | 5.7 |
| $C_{10} : C_{10}$ | 6.3 | 11.2 | 12.6 | 12.1 | — |
| $C_{10} : C_{12}$ | 6.3 | 13.5 | 13.3 | 12.5 | 5.7 |
| $C_{12} : C_{12}$ | 5.9 | 13.4 | 12.6 | 12.3 | 5.7 |

The 5% by weight concentration of the solution of detergents and detergent complexes used in the Mixmaster test described above was chosen since 5% is about the optimum concentration of these ingredients in a hair colorant/shampoo system, although a range of from about 1 to about 10% is acceptable.

Table 1 shows that the greatest foam volumes were obtained at detergent molar ratios of 50:50 and 60:40 anionic:cationic and it is preferred that these ratios are used in the compositions of the invention although ratios of from about 63:35 to about 35:65 anionic:cationic can be tolerated without much disadvantage.

Typical of the anionic-cationic complexes which can be used in the compositions of the invention are those formed between anionic detergents such as sodium and potassium soaps, especially those having chain lengths of from $C_8$-$C_{12}$ such as potassium laurate and potassium decanoate, alkyl and alkaryl sulphates and sulphonates such as sodium lauryl sulphate and sodium dodecyl benzene sulphonate, and tricarboxylic acid detergents. Cationic detergents can be chosen from, for example, $C_8$-$C_{18}$ alkyltrimethylammonium salts such as cetyltrimethylammonium bromide, lauryltrimethyl ammonium bromide and Arquad 12 (Trade Mark, a $C_{12}$ quaternary ammonium salt manufactured by Armour Hess Limited); diquaternary amine salts such as Duoquad T (Trade Mark, a diquaternary ammonium salt), derived from a long-chain aliphatic diamine and manufactured by Armour Hess Chemicals Limited and having the structure

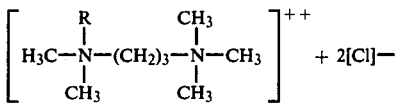

wherein R represents the long-chain aliphatic radical derived from tallow which is composed of approximately the following carbon chain lengths, $C_{16}$:29%, $C_{18}$(sat.):23%; $C_{18}$(unsat.):47% alkylpyridinium chlorides such as lauryl pyridinium chloride and ethoxylated quaternary ammonium salts.

The basic dyestuffs which are preferred in the compositions of this invention generally belong to the thiazole, acridine, polymethine, azine, triphenylmethane, oxazine, thiazine or anthraquinone types.

Specific examples of some dyestuffs which have been found to give acceptable coloration areas follow. These are identified by their trade names, and the color group to which they belong to the Color Index, published by the Society of Dyers and Colourists, Bradford, England, together with the Color Index Number where one has been allotted.

| Trade Name | Color Group | Color Index No. |
|---|---|---|
| Astra Blue 3R | Basic Blue 52 | — |
| Astrazon Yellow GRL | Basic Yellow 29 | — |
| Astrazon Golden Yellow GL | Basic Yellow 28 | — |
| Astrazon Red BL | Basic Red 45 | — |
| Astrazon Red RL | Basic Red 25 | — |
| Astrazon Red GTL | Basic Red 18 | — |
| Astrazon Blue B | Basic Blue 5 | 42140 |
| Astrazon Blue FRR | Basic Blue 69 | 42025 |
| Astrazon Blue G | — | — |
| Basacryl Yellow 3RL | Basic Orange 40 | — |
| Basacryl Yellow 5GL | Basic Yellow 24 | — |
| Basacryl Red FB | — | — |
| Basacryl Red FL | Basic Red 50 | — |
| Basacryl Red GL | Basic Red 29 | — |
| Basacryl Red XBL | Basic Red 51 | — |
| Deorlene Fast Yellow 7GL | Basic Yellow 21 | — |
| Deorlene Orange 2GL | Basic Orange 43 | — |
| Deorlene Fast Red 1GL | Basic Red 54 | — |
| Deorlene Fast Blue BL | Basic Blue 22 | — |
| Deorlene Blue BL | — | — |
| Deorlene Blue 5G | Basic Blue 3 | 51005 |
| Deorlene Blue BR | Basic Blue 49 | — |
| Diacryl Supra Brilliant Red 2G | Basic Red 61 | — |
| Diacryl Brilliant Red 2G-F | Basic Red 27 | — |
| Diacryl Brilliant Blue 2E | Basic Blue 85 | — |
| Enchrysine GGNX | Basic Yellow 9 | 46040 |
| Maxilon Blue GRL | Basic Blue 41 | — |
| Safranine TN125 | Basic Red 2 | 50240 |
| Sevron Brilliant Red B | Basic Red 15 | — |
| Sevron Red L | Basic Red 17 | — |
| Sevron Blue 5G | Basic Blue 4 | 51004 |
| Sevron Blue 4B | — | — |
| Thioflavine TCN | Basic Yellow 1 | 49005 |
| Methylene Blue | Basic Blue 9 | 52015 |
| Victoria Blue R | Basic Blue 11 | 44040 |
| Victoria Blue FBR | Basic Blue 55 | — |

Thioflavine TCN and dyes sold under the Trade Mark "Sevron" are available from E. I. du Pont de Nemours & Co. Inc. Wilmington, Del. USA. Dyes sold under the trade Victoria and the Trade Mark "Basacryl" are available from Badische Anilin & Soda Fabrik A.G., Ludwigshafen a Rhein, Germany. Dyes sold under the Trade Marks "Aztrazone," "Astrazon" and "Astra" are available from Farbenfabriken Bayer A.G., Leverkusen, Germany. Dyes sold under the Trade Marks "Maxilon" and "Deorlene" are available from Ciba-Geigy Limited, Basle, Switzerland. Safranine TN125 is available from Imperial Chemical Industries Limited, Dyestuffs Division, Manchester, England.

In general, it can be said that those colorant compositions which dye blonde Italian "Blue String" hair at a liquor ratio of 2:1 (dye solution to hair (w/w)) to give an L value of about 45 or lower are preferred compositions according to the invention. It will be understood that even though certain dyestuffs, particularly the yellow-colored ones, are incapable by themselves of producing hair having an L value of about 45 or less, they may be blended with other more intense dyes to produce a brown or black colorant which can meet the intensity requirement.

As mentioned above we have discovered that in certain circumstances the L value produced by a dye dissolved in an anionic-cationic detergent complex solution can be lower than that produced by a dye dissolved in a solution containing uncomplexed anionic or cationic detergents. The following table shows this effect demonstrated by the L values of three different dyestuffs dissolved at a level of 1%, both in a $C_{12}$ potassium soap —$C_{12}$ quaternary ammonium salt complex solution and in solutions of the components of the complex.

The intensity of the coloration produced by the dyestuff is measured in terms of the L co-ordinate value of the Adams Chromatic Value System as described in "Colour in Business, Science and Industry," by Judd & Wyszecki published by J. Wiley & Sons (1963). Spectral reflectance curves are measured on a Bausch and Lomb Spectronic 505 Ultraviolet spectrometer on chopped hair (in order to eliminate the specular components). The white reference substandard used is a clean titanium dioxide surface. L a b values are calculated using the C.I.F. 10° observer and C.I.E. Standard Illuminant C. Hair switches are made from Italian "Blue String" virgin blonde hair which is dyed at room temperature at a 2:1 liquor ratio (dye:hair w/w) for 20 minutes.

It should be noted that all solutions contained 8% by weight of isopropanol, since we have observed that the decrement in the L value of the dyestuff in the presence of the anionic-cationic detergent complex is reduced the greater the concentration in the solution of isopropanol.

Table 2

| Dyestuff | L An. | L50/50 | L Cat. |
|---|---|---|---|
| Deorlene Fast Red 2GL | 30 | 38.2 | 41 |
| Sevron Brilliant Red B | 48.4 | 39.0 | 42 |
| Deorlene Fast Blue BL | 51.5 | 45.5 | 48.3 |

That this unexpected effect is observable in a variety of detergent complexes is demonstrated in the following table, which shows the L value of a 1% solution of Deorlene Red 2GL in various detergents and detergent complexes. In most cases either isopropanol or the nonionic detergent Antarox CO 630 (Trade Mark), a nonylphenyl condensate with polyoxyethylene having an average molar concentration of 9 ethylene oxide units, manufactured by the GAF Corporation, was added to effect complete solution.

Table 3

|  | Arquad 12 | | | Duoquad T | | | Lauryl pyridinium chloride | | |
| --- | --- | --- | --- | --- | --- | --- | --- | --- | --- |
|  | LAn. | L50/50 | LCat. | LAn. | L50/50 | LCat. | LAn. | L50/50 | LCat. |
| Potassium laurate | 39 | 38.2 | 41 | 39 | 35.3 | 38.4 | 39 | 36.8 | 45 |
| Sodium dodecylbenzene sulphonate | — | — | — | 59.9 | 44 | 46.9 | — | — | — |
| Lauryl polyglycol sulphosuccinate | 31 | 43 | 44 | 57 | 47 | 48.3 | — | — | — |

It can be seen that in some instances very pronounced reductions in L value (increase in dyeing intensity) are achieved by using the 50/50 anionic-cationic detergent complex. Good results are achieved in this respect when the composition comprises a solution of one or more approximately equimolar anionic-cationic detergent complexes selected from complexes formed between a soap of a $C_8$–$C_{12}$ fatty acid, e.g. potassium laurate, sodium dodecylbenzene sulphonate and Condanol (Trade Mark), lauryl polyglycol sulphosuccinate manufactured by Dutton and Reinisch on the one hand and Arquad 12 (Trade Mark). Douquad T (Trade Mark), a di-quaternary ammonium salt derived from a long-chain aliphatic diamine and manufactured by Armour Heiss Chemicals Limited, cetyl trimethyl ammonium bromide and lauryl pyridinium chloride on the other and a dye selected from Deorlene Red 2GL, Sevron Brilliant Red B, Deorlene Fast Blue BL, Sevron Blue 5G, Basacryl Yellow 3RL, Deorlene Yellow 7GL and mixtures thereof.

We have found that some of the basic dyestuffs are insufficiently soluble in solutions of the anionic-cationic detergent complexes and so we have found it necessary to add a solvent such as isopropanol to ensure dissolution. Our compositions can include as much as 25% of isopropanol. The preferred range is from about 1 to about 10%.

We have also discovered that the hair-cleaning effect of the shampoo/colorant composition is improved by the addition of a nonionic surfactant to the anionic-cationic detergent solution.

Accordingly, the present invention further provides a high foaming composition for dyeing keratinous fibres comprising a solution of an anionic-cationic complex, a nonionic surfactant and a basic dyestuff.

A typical example of such a nonionic surfactant is the octyl phenol ethylene oxide condensate having an average molar concentration of 11 ethylene oxide units known as Nonidet P80 (Trade Mark, Shell Chemicals Ltd). The compositions may contain up to 20% of the nonionic surfactant, although normally not more than 15% will be used, and from 2 to 8% is preferred. The nonionic surfactant has also been found to increase the solubility of the basic dyes in the detergent solutions.

The formulations illustrated in the following Examples 1 and 2 were prepared by the following procedure. The dyes were dissolved in 50 g of water using rapid stirring, and the pH of the resulting solution was adjusted with dilute acetic acid or potassium hydroxide solution to 5.8. The surface-active agents were dissolved in the remainder of the water with very slow stirring in order to avoid aeration. Isopropanol was added and then the pH of the solution was adjusted using the same reagents to 6.4. The thickener was then added to the dye solution, using very fast stirring and slow addition of the powder in order to prevent the formation of lumps. The stirring was continued until the mixture was very thick and smooth. The detergent solution was then added dropwise to the thickened dye solution, slow stirring being maintained until all the solution had been added. The pH of the resulting solution was about 6 and the viscosity after standing was between 2,000 and 8,000 cps.

|  | % by weight |
| --- | --- |
| Maxilon Blue GRL (500%) | 0.3 g |
| Basacryl Red FB | 1.0 g |
| Deorlene Yellow 7GL | 1.2 g |
| Deorlene Orange 2GL | 0.3 g |
| Potassium laurate | 2.3 g  \} 0.552:1.000 molar ratio |
| Lauryl trimethyl ammonium bromide | 5.4 g |
| Tergitol NP 35 | 6.0 g |
| Isopropanol | 10.0 g |
| Carboxymethyl cellulose thickener | 3.2 g |
| Water | to 100 g |

Tergitol NP 35 (Trade Mark), a nonyl-phenol condensate with polyoxyethylene having an average molar concentration of 15 ethylene oxide units, is a nonionic surfactant manufactured by the Union Carbide Corporation.

EXAMPLE 2

|  | % by weight |
| --- | --- |
| Maxilon Blue GRL (500%) | 0.2 g |
| Basacryl Red FB | 1.0 g |
| Deorlene Yellow 7GL | 1.2 g |
| Deorlene Orange 2GL | 0.3 g |
| Potassium laurate | 2.25 g \} 0.828:1.000 molar ratio |
| Lauryl trimethyl ammonium bromide | 3.5 g |
| Nonidet P80 | 8.0 g |
| Isopropanol | 10.0 g |
| Carboxymethyl cellulose thickener | 2.8 g |
| Water | to 100 g |

EXAMPLE 3

This is an Example of an aerosol hair colorant composition in accordance with the invention.

|  | % by weight |
| --- | --- |
| Maxilon Blue GRL | 0.4 g |
| Deorlene Yellow 7GL | 2.0 g |
| Basacryl Red FB | 1.0 g |
| Basacryl Red GL | 1.0 g |
| Potassium laurate | 2.3 g |

-continued

|  | % by weight |
|---|---|
| Lauryl trimethyl ammonium bromide | 3.5 g |
| Tergitol NP35 | 6.0 g |
| Isopropanol | 10.0 g |
| Propellant 12 (dichlorodifluoromethane) | 6.0 g |
| Propellant 114 (Sym-dichlorotetrafluoroethane) | 6.0 g |
| Water | to 100.0 g |

We have found compositions such as these to give high foaming, high intensity dyeing and good cleaning of the hair.

Additionally these high foaming compositions have been found to be stable on storage and to give level dyeing of hair that has been permanent-waved.

It is to be understood that although it is preferred that the high foaming compositions of the present invention should be formulated as fairly viscous creams which are of a suitable consistency for dispensing from collapsible tubes, other forms of compositions are not excluded from the invention. In particular, as illustrated above, the compositions may be prepared in aerosol form.

What is claimed is:

1. An aqueous high foaming composition for dyeing hair comprising:
   (i) a sufficient amount of a basic dyestuff to impart color to said hair;
   (ii) from about 1 to about 10% by weight of an anionic-cationic detergent complex having a molar ratio of anionic to cationic detergent of from about 65:35 to about 35:65;
   (iii) from about 2 to about 8% by weight of a nonionic surfactant; and
   (iv) from about 1 to about 10% by weight of isopropanol.

2. A composition according to claim 1 wherein the anionic component of the complex is selected from the group consisting of a sodium soap, a potassium soap, an alkylsulphate, and an alkaryl sulphonate.

3. A composition according to claim 1 wherein the cationic component of the complex is selected from the group consisting of a $C_8$–$C_{18}$ alkyltrimethyl ammonium salt, a diquaternary amine salt, an ethoxylated quaternary ammonium salt and an alkylpyridinium chloride.

4. A composition according to claim 1 additionally comprising an aerosol propellant.

* * * * *